United States Patent [19]

Hennequin et al.

[11] Patent Number: 5,033,840
[45] Date of Patent: Jul. 23, 1991

[54] INTERPUPILLARY DISTANCE MEASURING DEVICE WITH NO MOVING PARTS

[75] Inventors: Jean-Claude Hennequin, Lizy-sur-Ourcq; Christian Massart, Clichy-Sous-Bois, both of France

[73] Assignee: Essilor International, Cie Generale d'Optique, Creteil, France

[21] Appl. No.: 512,400

[22] Filed: Apr. 23, 1990

[30] Foreign Application Priority Data

Apr. 25, 1989 [FR] France .................. 89 05478

[51] Int. Cl.⁵ .................................. A61B 3/10
[52] U.S. Cl. ......................... 351/204; 351/209
[58] Field of Search ........... 351/204, 202, 209, 211, 351/243

[56] References Cited

U.S. PATENT DOCUMENTS

| | | | |
|---|---|---|---|
| 4,591,246 | 5/1986 | Cousyn et al. | 351/204 |
| 4,712,895 | 12/1987 | Kamiyama et al. | 351/204 |
| 4,881,806 | 11/1989 | Bovet | 351/204 |

FOREIGN PATENT DOCUMENTS

| | | |
|---|---|---|
| 0305238 | 3/1989 | European Pat. Off. . |
| 8812095 | 12/1988 | Fed. Rep. of Germany . |
| 1506352 | 12/1967 | France . |
| 2620927 | 3/1989 | France . |
| 2152232 | 7/1985 | United Kingdom . |

*Primary Examiner*—Paul M. Dzierzynski
*Attorney, Agent, or Firm*—Charles A. Brown

[57] ABSTRACT

An interpupillary distance measuring device comprises a box with a front panel whose position corresponds to an eyeglass frame. The device has a main axis perpendicular to the front panel and equidistant from the eyes of the subject. A horizon plane perpendicular to the plane of the face passes through the main axis and the eyes of the subject. In the box are a master lens and a point light source at the focus of the lens and on the main optical axis. The point source creates at the center of the eyes of the subject corneal reflections, virtual images of which are formed by the lens. These virtual images form real objects for an objective lens which forms a pair of real images on a measurement scale formed by one or more linear arrays of photosensitive charge transfer devices. The device scans sequentially to identify the elements of the arrays at which the images are formed by means of the rank of those elements.

9 Claims, 3 Drawing Sheets

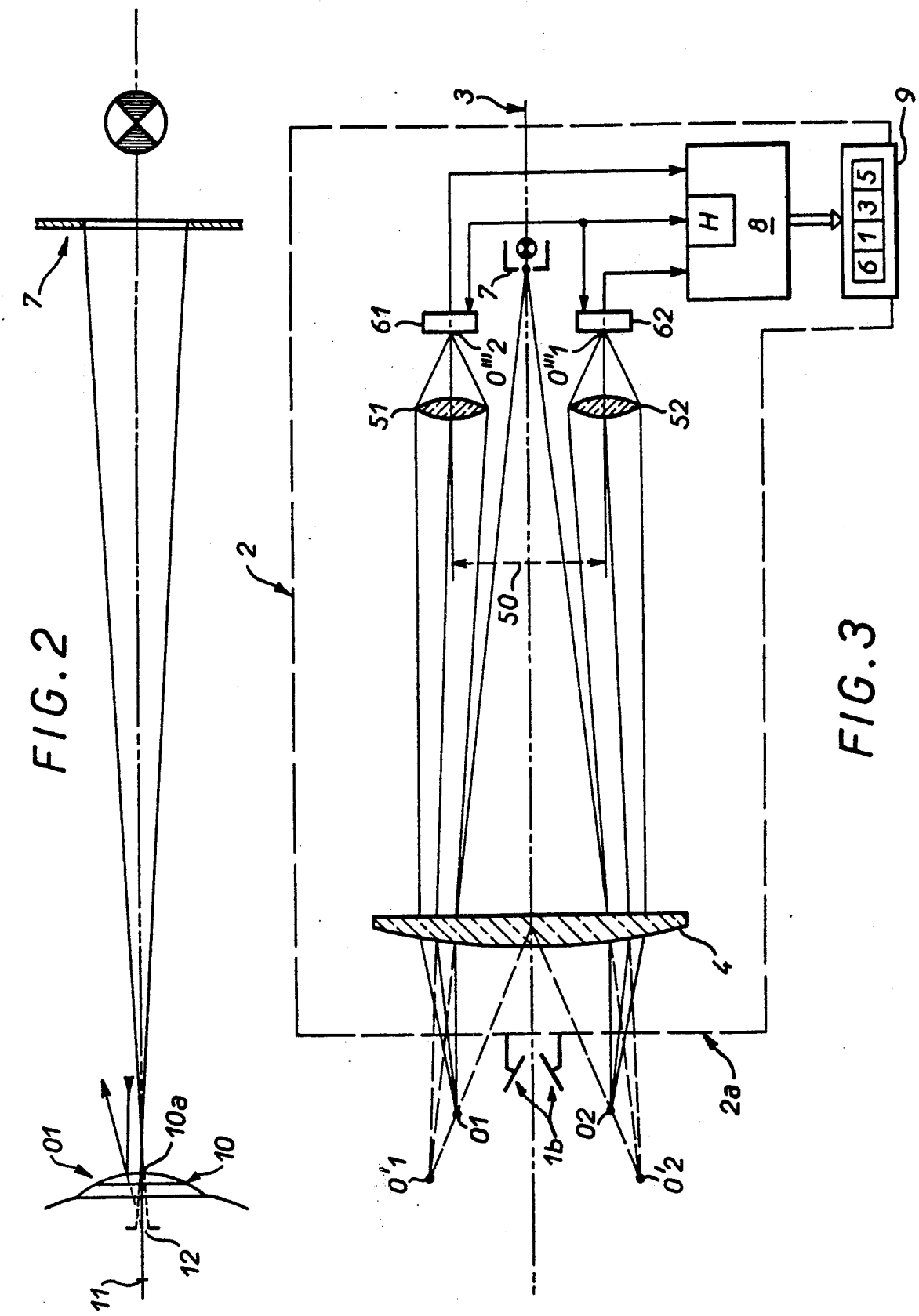

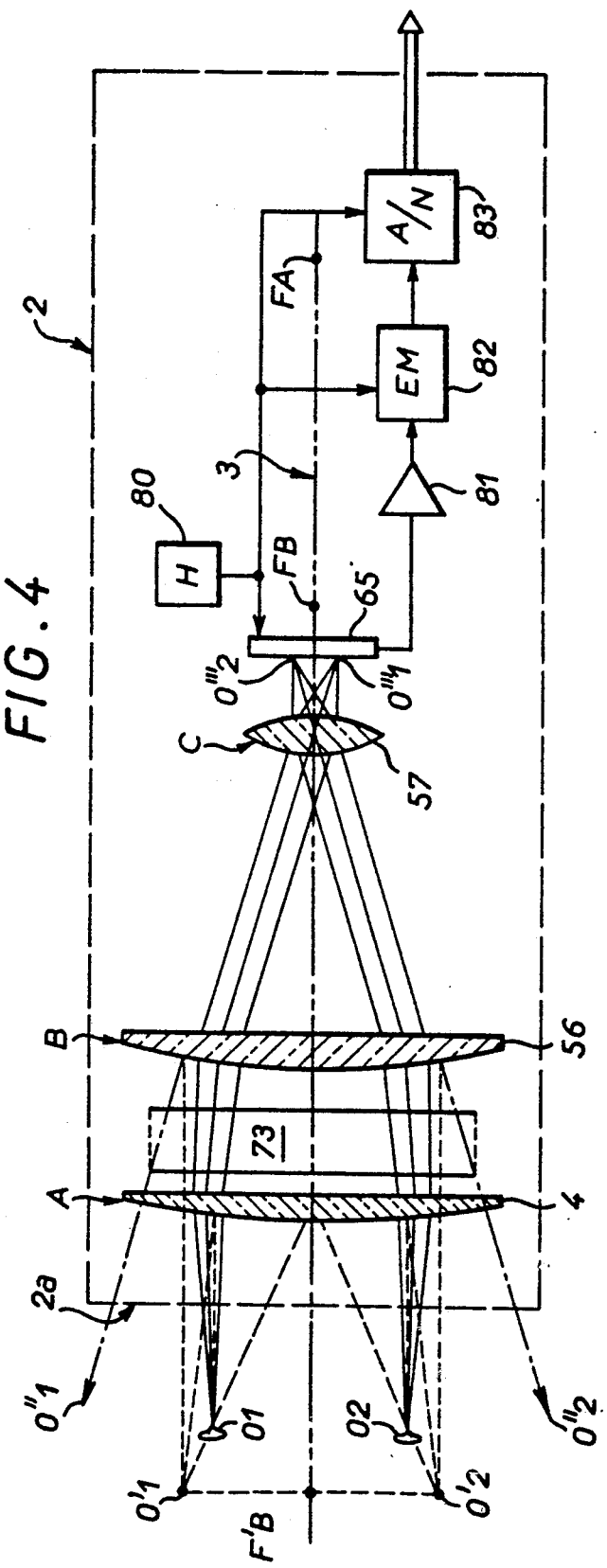
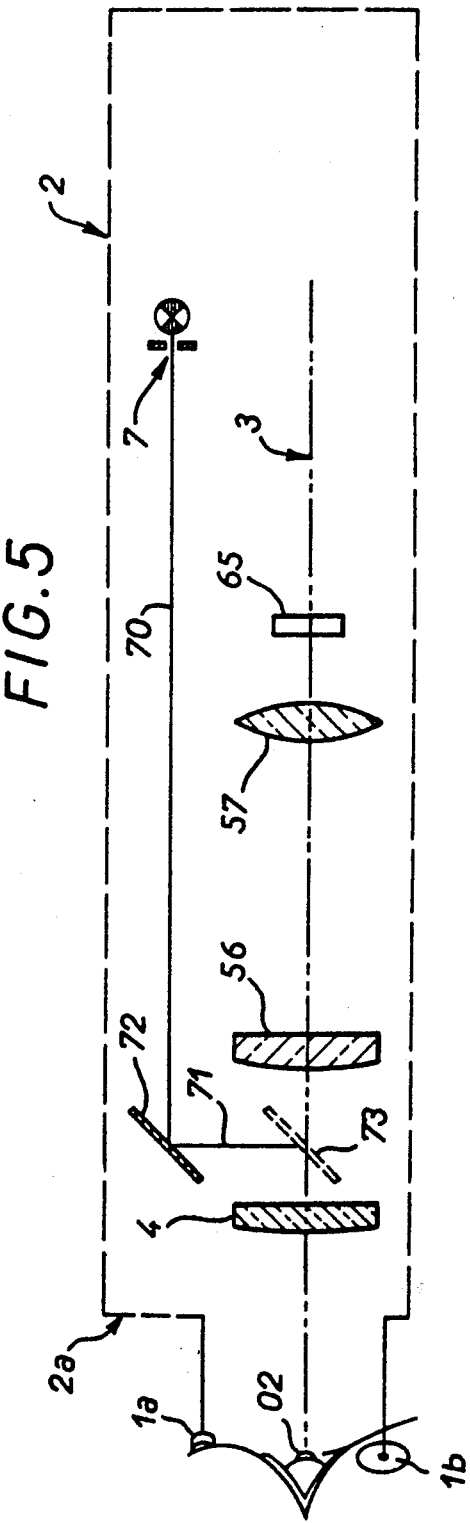

INTERPUPILLARY DISTANCE MEASURING DEVICE WITH NO MOVING PARTS

BACKGROUND OF THE INVENTION

1. Field of the Invention

The invention concerns a device for measuring the interpupillary distance of a person, for example to assist with fitting eyeglass frames, comprising a box; a generally flat front panel of said box adapted to be applied to the face of a person in a known relative position so that a main axis normal to said front panel and a horizon plane containing said main axis respectively pass equidistantly between and through the centers of the eyes of said person which are at a fixed distance from said front panel; windows in said front panel adapted to be aligned with the eyes of said person; a convergent master lens in said box near said front panel with its optical axis coincident with said main axis; a point light source optically on said main axis at a position such that it determines for said person viewing it through said master lens a determined observation distance, light emitted by said point source forming respective corneal reflections on the corneas of said person; a measuring scale in said horizon plane normal to said main axis, optical images of said corneal reflections coinciding with respective divisions on said scale; means for identifying said respective divisions; and means for calculating and displaying an interpupillary distance corresponding to an identified pair of divisions.

It will be noted that the main axis of the device is normal to the general plane of the face of the person and that the horizon plane is referred to the attitude of the person with the head held straight and with the gaze focused on the horizon. Also, the front panel substantially corresponds to the normal position of the eyeglass lenses.

2. Description of the Prior Art

Patent document FR-A-1 506 352 describes an interpupillary distance measuring device which comprises the basic optical system, namely the convergent master lens and a point source optically on the main axis of the box to define an observation distance for the person and to form spots of light at the center of the corneas of the person. In this interpupillary distance measuring device the master lens is movable along the main optical axis from an origin position near the front panel at which the point source is optically at the focus of the master lens, which corresponds to an infinite observation distance. An eyepiece is formed in the box on the main axis opposite the front panel, optically coincident with the point source. Two alidades with a vertical line are disposed substantially in the plane of the front panel and are movable in the horizon plane. An observer viewing through the eyepiece aligns the vertical lines of the alidades with the respective corneal reflections. Graduated rules fastened to the alidades enable the interpupillary distance to be read off.

This interpupillary distance measuring device, the optical design of which is excellent, suffered from lack of precision in the maneuvering of the alidades and in the reading of the graduated rules. The patent document U.S. Pat. No. 4,591,246 describes an interpupillary distance measuring device comprising the same basic optical system in which the alidades are replaced by liquid crystal matrices at least the columns of which are addressable. A column that is turned on causes a vertical line to appear, the address of the column being representative of the abscissa of the line along the intersection of the plane of the front panel and the horizon plane. The observer moves the vertical line by causing the address generators to be incremented or decremented. A microprocessor controlling all of the electronic circuitry converts into the interpupillary distance the difference between the abscissas of the vertical lines, represented by the corresponding column addresses, allowing for the distance between the two matrices and their pitches. The interpupillary distance is displayed on a digital display device. It will be noted that if the liquid crystal matrices rows can also be addressed this interpupillary distance measuring device can be used to determine the position in a vertical plane of the bottom part of an eyeglass frame relative to the center of the cornea.

The accuracy and ease of use of this interpupillary distance measuring device are significantly improved as compared with the interpupillary distance measuring device of document FR-A-1 506 352; however, it still requires action by an observer to adjust the coincidence of the vertical lines on the measuring scale with the images of the corneal reflections, especially as the coincidence for the right eye and that for the left eye must be adjusted independently of each other. Apart from errors due to the individual skill of the observer, distractions may cause the person to shift their gaze from the image of the point source during the adjustment, jeopardizing the accuracy of the measurement.

It was therefore seen to be desirable to have available an interpupillary distance measuring device capable of determining the coincidence of the images of the corneal reflections with divisions on a measuring scale and of displaying the interpupillary distance without an observer having to take part in the measurement process.

The patent document U.S. Pat. No. 4,881,806 describes an automatic interpupillary distance measuring device in which there is formed for each eye an array of corneal reflections with parallel lines of light perpendicular to the horizon plane, with an associated position reference. A combination of lenses and point sources defines an observation distance for the subject. A rotating mirror is optically coincident with the point source, its rotation axis being perpendicular to the horizon plane. The images of the corneal reflections and the position references, as captured by the rotating mirror and appropriately focused, are scanned across a slit parallel to the axis of the mirror in a mask behind which is located a photo-electric sensor. Analyzing the signal supplied by the photo-electric detector makes it possible to locate the corneal reflections relative to the position references. It will be noted that, in practise, and for each eye, only the corneal reflection corresponding to the line of the array nearest the center of the cornea forms an image captured by the rotating mirror, given the divergent nature of the mirror formed by the cornea.

This interpupillary distance measuring device does not require any adjustment of cross-hairs or alidades by an observer and is therefore automatic or "impersonal", the latter expression meaning that it does not depend on the individual skill of an observer. However, it requires the use of a mirror rotating at a regular speed: also, the processing of the signals from the photo-electric sensor is relatively complex given that the sensed measurement reference is memorized in a first phase and the corneal reflections are located relative to the memorized reference in a second phase.

The patent document FR-A-2 620 927 describes apparatus for measuring the parameters needed to fit optical lenses to a frame. This apparatus essentially comprises an optical camera using charge transfer photosensitive elements, a telemetry device for recording the distance from the subject to the camera and a computer with associated software. An image of the face of the subject wearing the eyeglass frame is formed and the distance from the subject to the camera is recorded to define the scale of the image. The image signals are processed by the computer to extract from them the relevant parameters. The actual measurement process is in fact carried out by the software, no description of which is given.

An object of the invention is an interpupillary distance measuring device using for the most part the basic optical system from FR-A-1 506 352 and U.S. Pat. No. 4,591,246 but which is automatic and therefore impersonal, in the sense explained above and furthermore has no moving parts.

SUMMARY OF THE INVENTION

The invention consists in a device for measuring the interpupillary distance of a person, for example to assist with fitting eyeglass frames, comprising a box; a generally flat front panel of said box adapted to be applied to the face of a person in a known relative position so that a main axis normal to said front panel and a horizon plane containing said main axis respectively pass equidistantly between and through the centers of the eyes of said person which are at a fixed distance from said front panel; windows in said front panel adapted to be aligned with the eyes of said person; a convergent master lens in said box near said front panel with its optical axis coincident with said main axis; a point light source optically on said main axis at a position such that it determines for said person viewing it through said master lens a determined observation distance, light emitted by said point source forming respective corneal reflections on the corneas of said person; a measuring scale in said horizon plane normal to said main axis, optical images of said corneal reflections coinciding with respective divisions on said scale; means for identifying said respective divisions; means for calculating and displaying an interpupillary distance corresponding to an identified pair of divisions; an objective lens adapted to form in an image plane containing said scale a pair of real images of said corneal reflections viewed through said master lens; at least one photo-electric device in said scale comprising an array of sensitive members constituting scale divisions; and means for sequentially scanning said array to determine the rank therein of the members at which said positive images of said corneal reflections are formed.

In this device the measurement scale is physically stable and the objective lens determines a stable relationship between the interpupillary distance and the distance between the real images on the measuring scale. The array of photo-electric sensitive members is scanned sequentially without using any moving parts.

Given that the interpupillary distance for near vision can be accurately deduced from the interpupillary distance with the gaze fixed at infinity, because the distance between the center of rotation of the eye and the cornea varies to only a limited extent from one person to another and introduces only second order variations in the interpupillary distance for near vision, the point source will generally be optically at the focus of the master lens.

In a preferred embodiment the photo-electric device is a semiconductor charge transfer device in which an array of suitably biased field grids forms an array of potential wells in which accumulate charge carriers formed by the impact of photons on an neighboring region of a photosensitive target. Scanning is performed by applying streams of pulses to the field grids causing the walls of the potential wells to move in the scanning direction in steps equal to the array increment. The charges accumulated between two scans in the potential wells are thus transferred sequentially into a scanning region where they create a signal whose amplitude represents the charge accumulated in each potential well and whose rank in the scan represents the rank of the position of the potential well in question.

With a view to simplicity, the charge transfer device is preferably a linear array. Where the only requirement is to measure the interpupillary distance, no purpose would be served by using a two-dimensional matrix charge transfer device requiring double scanning, similar to the scanning of a television signal.

In a first embodiment the objective lens comprises a pair of convergent lenses disposed symmetrically relative to said main axis and each having an optical axis in said horizon plane parallel to said main axis, the device comprising a respective photo-electric device and array of photosensitive members associated with each lens.

The distance between the optical axes of the lenses of the objective lens will normally be set to the population average interpupillary distance. The images of the corneal reflections focused onto the photo-electric arrays will depart from the optical axes of the lenses of the objective lens by an angle, as seen from the optical center of the lens, equal to the angle, as seen from the same optical center, between the optical axis of the objective lens and the ray from the virtual image of the corresponding corneal reflection formed by the master lens. This embodiment therefore essentially determines the difference between the actual interpupillary distance of the person and the selected value of population average interpupillary distance.

In another embodiment the objective lens comprises a convergent entry lens having an optical axis coincident with said main axis at a distance from said master lens such that the convergent combination of said entry and master lenses has a focal plane parallel to said front panel at said fixed distance from the eyes to the panel and a convergent exit lens having an optical axis coincident with said main axis, the device comprising a photo-electric device with an array of photosensitive members in a focal plane of said exit lens on the side thereof opposite said entry lens.

This embodiment uses a single photo-electric device onto which is projected an image of the face of the subject showing only the corneal reflections. The device actually measures the interpupillary distance, with a predetermined scale factor, rather than determining the difference between the actual interpupillary distance and the population average interpupillary distance. Although in this second embodiment the random error, resulting from lack of precision as to the rank of the photosensitive elements concerned is higher than that of the first embodiment, there is no systematic error resulting from lack of precision as to the distance between the optical axes of the lenses of the objective lens.

In the second embodiment the three lenses are centered on the main axis. The point source must therefore be physically offset from the main axis. The device therefore preferably comprises a semi-reflecting mirror between said master lens and said entry lens at an angle to said horizon plane which it intersects on a normal to said main axis to define a main reflected ray corresponding to a ray from said master lens passing along said main axis, in which device said point source is optically on said main reflected ray at a point conjugate with the focus of said master lens.

In this case, the device preferably comprises a plain mirror parallel to said semi-reflecting mirror on the optical path of said main reflected ray, and said point source is physically on said ray, parallel to the main axis of said main reflected ray.

The semi-reflecting mirror is preferably at 45° to the horizon plane.

Secondary characteristics and advantages of the invention will emerge from the following description given by way of example only and with reference to the appended diagrammatic drawings.

BRIEF DESCRIPTION OF THE DRAWINGS

FIG. 2 is a diagram showing how a corneal reflection is formed.

FIG. 3 is a cross-section on a horizon plane of a first embodiment of the invention.

FIG. 4 is a cross-section on a horizon plane of a second embodiment of the invention.

FIG. 5 is a cross-section on a vertical plane of the interpupillary distance measuring device from FIG. 4.

DETAILED DESCRIPTION OF THE INVENTION

Figure 1:
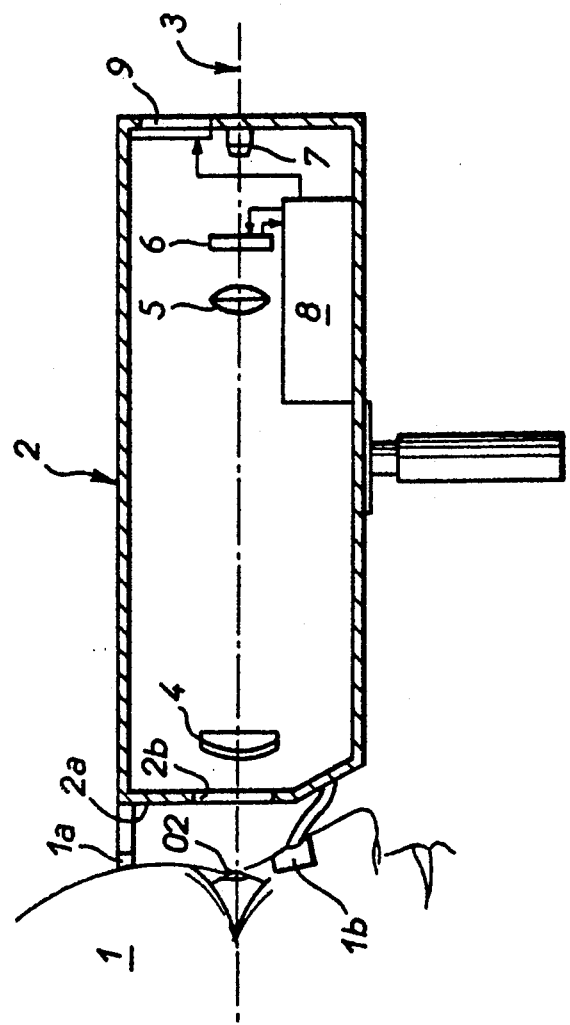
FIG. 1 is a schematic view in cross-section of an interpupillary distance measuring device in accordance with the invention.

In the embodiment shown in FIG. 1 the interpupillary distance measuring device comprises a box 2 with a generally flat front panel 2a perpendicular to a main axis 3. The front panel 2a carries a head support 1a and a set of nose pads 1b so that, when resting against the face of a subject 1, the front plate 2a is globally parallel to the face of the subject 1, the main axis 3 is equidistant from the eyes of the subject 1 and a horizon plane passing through the main axis and perpendicular to the plane of the figure passes through the center of the eyes (at 02 for the righthand eye of the subject, the only one visible in the figure).

The front panel 2a comprises windows 2b opposite the eyes of the subject and which substantially correspond to the location of the eyeglass lenses in the frame.

Inside the box 2 near the front panel 2a is a convergent lens referred to hereinafter as the master lens and the optical axis of which coincides with the main axis 3 of the interpupillary distance measuring device Its focus on the side opposite the front panel 2b coincides with a point light source 7 located against a surface parallel to and opposite the front panel 2a. It will be understood that, as viewed through the master lens 4 by the subject 1, the point light source appears to be at infinity, the visual rays from the eyes of the subject being parallel to the main axis 3.

The light emitted by the point source 7 is reflected at the center of the cornea of each eye of the subject 1 as a light spot, as will be explained with reference to FIG. 2.

The virtual images of the corneal reflections formed by the lens 4 constitute for an objective lens 5 real objects to which there correspond real images in a plane perpendicular to the main axis in which is located a measurement scale 6 also lying in the horizon plane. The measurement scale 6 comprises charge transfer devices with an array of photosensitive elements the content of which is scanned sequentially by a control and read-out device 8, computing means being provided to show the interpupillary distance. This will be described in detail with reference to FIGS. 3 through 6.

Referring to FIG. 2, the eye 01 comprises a cornea 10 projecting slightly from the eyeball and with the shape of a substantially spherical dome with its center at 11. Although transparent, the cornea 10 is partially reflecting and for external light rays constitutes a convex spherical mirror 10 the focus 12 of which is halfway between the center 11 and the summit 10a of the spherical dome. For this spherical mirror 10 the point source 7, to be more precise its image formed through the lens 4, is located at infinity. The image of the point source 7 formed by this spherical mirror 10 is located in its focal frame 12 with an aperture equal to the apparent aperture of the point source 7. To give a concrete example, if the point source has an aperture diameter of 2 mm and the master lens 4 has a focal length of 300 mm, taking a value of 9 mm for the radius of curvature of the cornea, that is a mirror focal length of 4.5 mm, the diameter of the virtual image in the plane 12 would be 0.03 mm.

In the embodiment shown in FIG. 3, in which the box 2 is shown in schematic outline, the left and right eyes of the subject are at the respective positions 01 and 02 when the face of the subject is placed against the front panel 2a with the nosepads 1b bearing on the subject's nose. The master lens 4 is located in the box 2 near the front panel 2a with its optical axis coincident with the main axis 3 of the interpupillary distance measuring device. The point source 7, shown as a line source behind an aperture, is located on the main axis 3 at the focus of the lens 4 on the side thereof opposite the front panel 2a. Viewing the point source 7 through the lens 4, the subject sees it at infinity and the optical axes of the eyes 01 and 02 are parallel to the main optical axis 3 and in the horizon plane, which is the plane of the figure in this case. The images of the point source 7 formed by the corneas of the subject are virtual images at 01 and 02, as explained with reference to FIG. 2.

For an (imaginary) observer on the same side of the lens 4 as the point source 7 the lens 4 produces from the corneal reflections 01 and 02 virtual images 0'1 and 0'2, respectively. To construct graphically the locations of the virtual images 0'1 and 0'2 it must be borne in mind that rays parallel to the axis from 01 and 02 are deflected to pass through the focus and that rays passing through the optical center of the lens 4 are not deflected. Thus 0'1 and 0'2 are aligned with 01 and 02 on straight lines passing through the center of the lens 4 and are aligned with the projection of 01 and 02 on the main plane of the lens 4 on straight lines passing through the focus 7.

An objective lens comprising two convergent lenses 51 and 52 disposed symmetrically relative to the main axis 3 with their optical axes in the horizon plane (the plane of the figure) and separated by a distance 50 produce from the real images 0'1 and 0'2, constituting real objects, real images 0'''1 and 0'''2, respectively, on a pair of respective charge transfer strips 61 and 62.

These strips lie in the horizon plane perpendicular to the main optical axis.

The real images 0'''1 and 0'''2 are aligned with the images 0'1 and 0'2 respectively on straight lines passing through the optical center of the lenses 51 and 52 respectively. The beams originating from the corneal reflections at 01 and 02, which converge at the charge transfer strips 61 and 62, are shown by their central and marginal rays.

The distance 50 is chosen to match the population average interpupillary distance. It will be noted that the objective lens is an inverting optical system so that the displacements 0'''1 and 0'''2 relative to the optical axis of the lenses 61 and 62 respectively are in the opposite direction to the offsets of 0'1 and 0'2 relative to these optical axes. It will be noted that the distance 50 is not the average value of interpupillary distance but the average value of the distance between the images 0'1 and 0'2, which allows for the magnification introduced by the master lens 4.

As has already been mentioned, charge carriers released in the semiconductor due to the impact of photons accumulate in the cells on which the real images 0'''1 and 0'''2 are formed. Sequential scanning of the content of the strip element potential wells in response to clock pulses 11 forms signals in which each signal element is characterized by its rank on the strip. Given the pitch of the strip array, sequential scanning identifies with the rank of the element at which the image 0'''1 and 0'''2 is formed the dimensional offset of the image relative to a centered origin.

It is therefore possible to calculate the interpupillary distance in a control and computing unit 11 from the following optical parameters: the identifiable magnification, the distance 50 between the lenses 51 and 52 of the objective lens and the rank of the cells on which the images 0'''1 and 0'''2 impinge, the interpupillary distance being shown on the display 9. It is also possible to calculate and display the distance between the center of each pupil and the main axis 3 if the eyes are not symmetrical. To give a concrete example, the lens 4 has a focal length of 250 mm and the lenses 51 and 52 focal lengths of 25 mm. The eyes 01 and 02 are 70 mm from the main plane of the lens. The optical centers of the lenses 51 and 52 are 200 mm from this main plane. The distance between the lenses 51, 52 and the charge transfer strips 61 and 62 is 27 mm. The magnification calculations use conventional formulas that are well known to those skilled in optics.

The embodiment shown in FIGS. 4 and 5 incorporates a single charge transfer strip 61 and all of the optics are centered on the main axis.

Inside the box 2 is a convergent master lens 4 or A the focus FA of which is on the main axis 3, this master lens being near the front panel. The point source 7 (see FIG. 5) is optically at the focus of the master lens 4, but is offset geometrically perpendicularly to the horizon plane (the plane of FIG. 4) by a semi-reflecting mirror 73 which intersects the horizon plane at 45° along a line perpendicular to the main axis 3 and by a mirror 72 parallel to the mirror 73 so that, as seen in a vertical plane (the plane of FIG. 5), the central ray of the optical path between the point source 7 and the master lens 4 is initially parallel to the main axis 3 as far as the mirror 72, then perpendicular (at 71) to the axis 3 between the mirror 72 and the semi-reflecting mirror 73, and coincident with the main axis 3 beyond this point. For the subject, whose left and right eyes are respectively at 01 and 02, the point source 7 appears at infinity on the main axis 3 in the horizon plane. For an observer on the side of the lens 4 opposite the front panel 2a the lens 4 produces from the corneal reflections at 01 and 02 virtual images at 0'1 and 0'2 respectively as already explained with reference to FIG. 3.

An objective lens comprises a convergent entry lens 56 or B of comparable size to the master lens 4 and whose optical axis coincides with the main axis 3; its focus is at FB. The semi-reflecting mirror is between the master lens 4 and the entry lens 56 of the objective lens. The focal length of the lens 56 and its distance from the master lens 4 are such that the optical system formed by the lenses 4 and 56 has a focal plane through the eyes 01 and 02 of the subject. It must be borne in mind that, optically speaking, the eyes are the corneal reflections. In other words the virtual images 0'1 and 0'2 of the corneal reflections 01, 02 formed by the lens 4 are in the focal plane of the entry lens 56 which intersects the main optical axis at F'B.

The lens 56 forms from the virtual images 0'1, 0'2 forming real objects images 0''1, 0''2 at infinity. The directions of these images 0''1, 0''2 at infinity can be determined graphically noting that rays parallel to the main axis 3 from 0'1 and 0'2 are refracted by the entry lens 56 to pass through FB.

The objective lens further comprises an exit lens 57 (or C) the optical axis of which coincides with the main axis 3. The exit lens 57 forms from the images 0''1, 0''2 at infinity real images 0'''1, 0'''2 in its focal plane, in which is a charge transfer strip 65 in the horizon plane (the plane of FIG. 4) and perpendicular to the main optical axis.

FIG. 4 shows the beams defined by the central ray and the marginal rays which start from the corneal reflections 01, 02 and extend to the charge transfer strips 65 and 0'''1 and 0'''2, respectively.

The ratio between the distance 0'''1-0'''2 and the interpupillary distance 01-02 is determined from the focal length of the lenses 4, 56 and 57 and from their positions on the main optical axis 3. In one example the distance between the eyes 01, 02 and the master lens 4 is 70 mm, the focal length of the lens 4 is 300 mm, the distance between the optical centers of the master lens 4 and the entry lens 56 of the objective lens is 50 mm, with a focal length of the entry lens 56 of 140 mm, the distance between the optical centers of the entry lens 56 and the exit lens 57 of the objective lens is 98 mm and the focal length of the exit lens 57 of the objective lens is 25 mm. With these values the magnification ratio is approximately 0.3. It will be noted that the distance between the optical centers of the entry lens 56 and the exit lens 57 of the objective lens plays only a second order role since the exit lens 57 produces images in its focal plane of objects at infinity and the distance between these images depends on the focal length and the angular separation of the objects 0''1, 0''2. The distance between the optical centers of the lenses of the objective lens is operative to distribute the obliqueness of the beams relative to the successively encountered optical surfaces and so reduce deterioration thereof.

The charge transfer strip 65 is scanned sequentially by transferring its potential well contents at the rate of timing pulses from the clock 80. The scanning signals are amplified and filtered at 80, shaped by a sample and hold circuit 82 and memorized for processing by a microprocessor by an analog-to-digital converter 83 which associates with them a rank address corresponding to the rank of the photosensitive element of the strip array 65.

Figure 6:
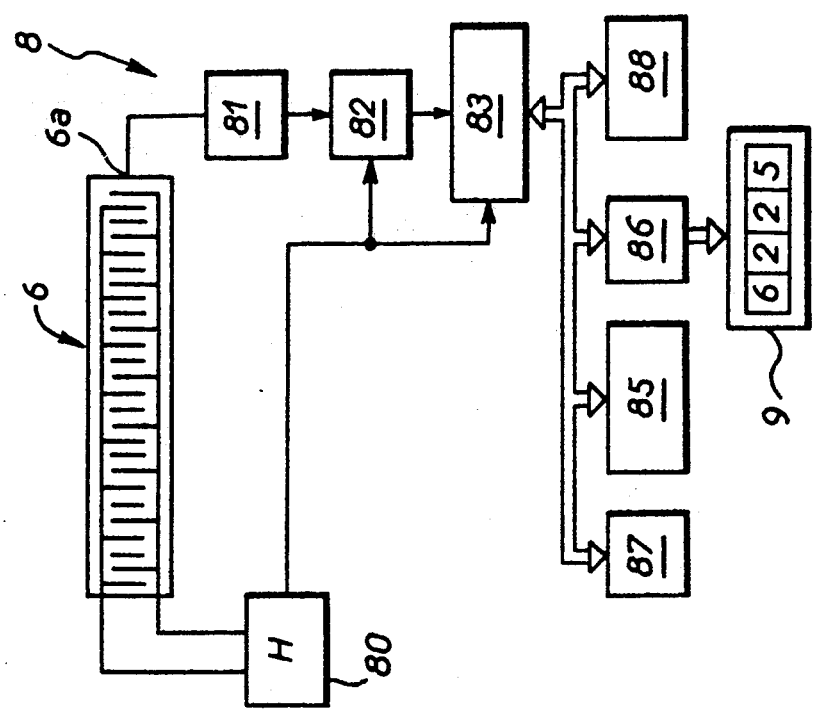
FIG. 6 is a schematic of the electronic circuitry associated with the optical systems of interpupillary distance measuring devices in accordance with the invention.

Referring to FIG. 6, it is seen that the clock 80, directs two streams of signals to the charge transfer strip which comprises two interleaved arrays which, with a suitably biased third array, form between them wells which expand by virtue of movement of their wall on the same side as the scanning region 6a and then contract by sliding movement of their other wall, moving forward by one step each time in this way.

As previously explained, the sequential arrival during the scanning phase of the charge carriers accumulated in the various potential wells during a previous accumulation phase in the scanning region supplies a signal temporally representative of the quantities of light received by each cell of the array in spatial sequence. This signal is amplified and filtered by a stage 81 and then shaped by a sample and hold stage 82 which is responsive to the input voltage during a short pulse at the clock timing rate and which holds the detected voltage until the next pulse. The converter 83 converts the analog signal delivered by the stage 82 into a digital signal associated with a rank address.

This complex digital signal is processed by a microprocessor 85 associated with a memory 87 and a display output 88 which is connected to a digital display. A selector 88 selects the necessary computing modes, checks and calibrations. All of the arrangements based on the microprocessor 85 are designed to make the interpupillary distance measuring device easy to operate and do not form any part of the present invention.

However, it goes without saying that non-volatile memory is used to store data such as the optical magnification, the pitch of the charge transfer strips and the distance between the axes of the lenses of the objective lens in the case of the FIG. 3 interpupillary distance measuring device. The description given is sufficiently detailed for those skilled in the art to be able to carry out all the necessary steps relating to exploitation of the determined coincidence of the corneal reflection images with the divisions on the measuring scale.

What is more, it goes without saying that the present invention is not limited to the examples described but encompasses all variant executions thereof within the scope of the claims.

In particular, the master lens 4 could be mobile parallel to the main axis 3 in order to measure the interpupillary distance for a near vision distance, rather than at infinity. The measuring scales could be implemented with photo-electric devices other than charge transfer devices, although charge transfer devices have a particularly beneficial sensitivity by virtue of the mechanism whereby charges accumulate in the potential wells.

Also the photo-electric devices used to implement the measuring scales, and in particular the charge transfer devices, could have a matrix structure of rows and columns. It would then be possible to measure, in addition to the interpupillary distance, the vertical distance between the bottom of the eyeglass frame and the corresponding corneal reflection.

We claim:

1. Device for measuring the interpupillary distance of a person, for example to assist with fitting eyeglass frames, comprising a box; a generally flat front panel of said box adapted to be applied to the face of a person in a known relative position so that a main axis normal to said front panel and a horizon plane containing said main axis respectively pass equidistantly between and through the centers of the eyes of said person which are at a fixed distance from said front panel; windows in said front panel adapted to be aligned with the eyes of said person; a convergent master lens in said box near said front panel with its optical axis coincident with said main axis; a point light source optically on said main axis at a position such that it determines for said person viewing it through said master lens a determined observation distance, light emitted by said point source forming respective corneal reflections on the corneas of said person; a measuring scale in said horizon plane normal to said main axis, optical images of said corneal reflections coinciding with respective divisions on said scale; means for identifying said respective divisions; means for calculating and displaying an interpupillary distance corresponding to an identified pair of divisions; an objective lens adapted to form in an image plane containing said scale a pair of real images of said corneal reflections viewed through said master lens; at least one photo-electric device in said scale comprising an array of sensitive members constituting scale divisions; and means for sequentially scanning said array to determine the rank therein of the members at which said positive images of said corneal reflections are formed.

2. Device according to claim 1 wherein said point source is optically at a focus of said master lens so that said observation distance is infinite.

3. Device according to claim 1 wherein said at least one photo-electric device is a semiconductor charge transfer device comprising an array of potential wells adapted to accumulate charge from an area contiguous with a photosensitive target and transfer grids adapted to respond to scanning pulses by transferring charges from well to well until they reach a scanning region.

4. Device according to claim 3 wherein said array of potential wells is a linear array.

5. Device according to claim 1 wherein said objective lens comprises a pair of convergent lenses disposed symmetrically relative to said main axis and each having an optical axis in said horizon plane parallel to said main axis, the device comprising a respective photo-electric device and array of photosensitive members associated with each lens.

6. Device according to claim 1 wherein said objective lens comprises a convergent entry lens having an optical axis coincident with said main axis at a distance from said master lens such that the convergent combination of said entry and master lenses has a focal plane parallel to said front panel at said fixed distance from the eyes to the panel and a convergent exit lens having an optical axis coincident with said main axis, the device comprising a photo-electric device with an array of photosensitive members in a focal plane of said exit lens on the side thereof opposite said entry lens.

7. Device according to claim 6 comprising a semi-reflecting mirror between said master lens and said entry lens at an angle to said horizon plane which it intersects on a normal to said main axis to define a main reflected ray corresponding to a ray from said master lens passing along said main axis, in which device said point source is optically on said main reflected ray at a point conjugate with the focus of said master lens.

8. Device according to claim 7 comprising a plane mirror parallel to said semi-reflecting mirror on the optical path of said main reflected ray, in which device said point source is physically on said ray, parallel to the main axis of said main reflected ray.

9. Device according to claim 7 wherein said semi-reflecting mirror is at 45° to said horizon plane.

* * * * *